United States Patent [19]

Hirako et al.

[11] Patent Number: 4,891,121
[45] Date of Patent: Jan. 2, 1990

[54] AIR FUEL RATIO DETECTING DEVICE

[75] Inventors: Osamu Hirako; Yoshiaki Danno; Makoto Shimada, all of Kyoto, Japan

[73] Assignee: Mitsubishi Jidosha Kogyo Kabushiki Kaisha, Tokyo, Japan

[21] Appl. No.: 79,329

[22] Filed: Jul. 30, 1987

[30] Foreign Application Priority Data

Jul. 30, 1986 [JP] Japan .................................. 61-179210

[51] Int. Cl.$^4$ ............................................ G01N 27/58
[52] U.S. Cl. ..................................... 204/406; 204/410; 204/412; 204/425
[58] Field of Search ............... 204/406, 410, 412, 425, 204/1 S

[56] References Cited

U.S. PATENT DOCUMENTS

| | | | |
|---|---|---|---|
| 4,578,171 | 3/1986 | Yamada et al. | 204/406 |
| 4,578,172 | 3/1986 | Yamada et al. | 204/412 |
| 4,591,421 | 5/1986 | Yamada et al. | 204/406 |
| 4,594,139 | 6/1986 | Asayama et al. | 204/410 |
| 4,601,809 | 7/1986 | Kitahara | 204/406 |
| 4,615,787 | 10/1986 | Yamada et al. | 204/406 |
| 4,707,241 | 11/1987 | Nakagawa et al. | 204/406 |

Primary Examiner—G. L. Kaplan
Attorney, Agent, or Firm—Schwartz & Weinrieb

[57] ABSTRACT

An air fuel ratio detecting device which is improved in accuracy as compared to similar prior art devices comprises a sensor cell for developing an electrical signal in response to the difference between the concentration of oxygen in the exhaust gas and the concentration of oxygen in a reference gas, a controlling means for developing an electrical control signal having a polarity determined from the output of the sensor cell, a pump cell for moving oxygen ions in response to the electrical control signal received from the controlling means, a control current detecting means for detecting control current flow between the controlling means and the pump cell, an air fuel ratio detecting means for detecting the air fuel ratio from the control current flow, a stoichiometric air fuel ratio detecting means for detecting the direction of the control current flow so as to determine the stoichiometric air fuel ratio, a storage means for storing therein a linear air fuel ratio value which is determined in a predetermined functional relationship with respect to the magnitude of the control current flow, a linear air fuel ratio detecting means for detecting the magnitude of the control current flow detected by the control current detecting means so as to compare the same with the stored linear air fuel ratio value from the storage means; and a correcting means for correcting the predetermined functional relationship stored in the storage means when a stoichiometric air fuel ratio signal is developed from the stoichiometric air fuel ratio detecting means.

15 Claims, 4 Drawing Sheets

AIR FUEL RATIO DETECTING DEVICE

FIELD OF THE INVENTION

This invention relates to a device for detecting the air fuel ratio with a high degree of accuracy of an air fuel mixture supplied to the combustion apparatus of an internal combustion engine.

BACKGROUND OF THE INVENTION

Various air fuel ratio detecting devices have been proposed which make use of characteristics of the oxygen concentration cell action and the oxygen ion pumping action of zirconia as disclosed, for example, in Japanese patent laid-open No. 56-130649. However, the accuracy of such conventional air fuel ratio detecting devices are not sufficiently high as to allow the air fuel ratio detecting devices to be used for detecting a stoichiometric air fuel ratio, such as, for example, for a ternary catalyzer, due to its structure.

Besides, in the case of an $O_2$ sensor used as a conventional type stoichiometric air fuel ratio detecting device, deviations from the stoichiometric air fuel ratio cannot be readily discriminated, and accordingly the width of the fluctuations in the feedback control of the air fuel ratio is comparatively great, which will cause variation in the output power of the engine or in the number of engine revolutions during idling of the internal combustion engine.

An air fuel ratio detecting device is disclosed in Japanese patent application No. 60-262982 corresponding to U.S. patent application Ser. No. 933,850 wherein a sensor cell detects the difference between the concentration of oxygen in the exhaust gas and the concentration of oxygen in a reference gas so as to develop a corresponding electrical signal. In response to the electrical signal, a controlling means produces and delivers an electrical controlling signal to a pump cell so that the pump cell may cause, in response to the electrical controlling signal received, movement of oxygen ions until the level of the air fuel ratio, and the time at which the stoichiometric air fuel ratio is reached, are detected by first and second detecting means from the information regarding the air fuel ratio as transmitted from the controlling means to the pump cell.

However, where an air fuel ratio detecting device of the aforementioned type is employed, there is the problem that the degree of accuracy of the device may be low due to a possible error between products or due to the fact that the device may deteriorate with time due to extensive use.

OBJECT OF THE INVENTION

It is therefore an object of the present invention to provide an air fuel ratio detecting device which exhibits improved accuracy as compared to the degree of operative accuracy characteristic of conventional air-fuel ratio detecting devices.

SUMMARY OF THE INVENTION

In order to attain the foregoing and other objects, according to the present invention, there is provided an air fuel ratio detecting device, comprising: a sensor cell for developing an electrical signal in response to the difference between the concentration of oxygen in an exhaust gas, after an air fuel mixture has been burned in a combustion chamber, and the concentration of oxygen in a reference gas; a controlling means for developing an electrical control signal having a polarity determined from the output of the sensor cell; a pump cell for moving oxygen ions in response to an electrical control signal received from the controlling means; a control current detecting means for detecting control current flow transmitted from the controlling means to the pump cell; a stoichiometric air fuel ratio detecting means for detecting the direction of the control current flow so as to determine the stoichiometric air fuel ratio; a storage means for storing therein a linear air fuel ratio value which is determined in a predetermined functional relationship with respect to the magnitude of the control current flow; a linear air fuel ratio detecting means for detecting the magnitude of the control current flow detected by the control current detecting means for comparison with the stored linear air fuel ratio value from the storage means; and a correcting means for correcting the predetermined functional relationship stored in the storage means when a stoichiometric air fuel ratio signal is developed from the stoichiometric air fuel ratio detecting means.

BRIEF DESCRIPTION OF THE DRAWINGS

Various other objects, features, and attendant advantages of the present invention will become more apparent when considered in conjunction with the accompanying drawings, in which like reference characters are used to designate corresponding parts throughout the several views, and wherein.

DETAILED DESCRIPTION OF THE PREFERRED EMBODIMENT

Figure 1:
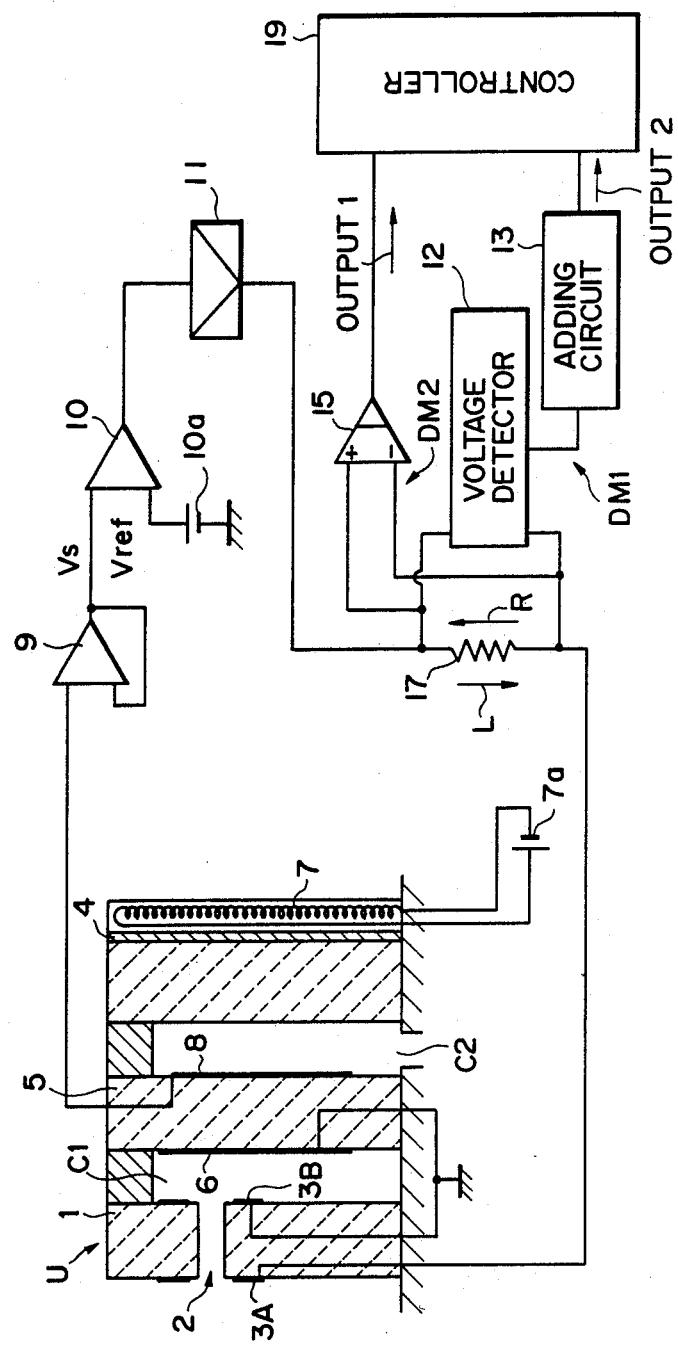
FIG. 1 is a diagrammatic representation illustrating the entire construction of an air fuel ratio detecting device according to a preferred embodiment of the present invention.

Referring first to FIG. 1, an air fuel ratio detecting device according to a preferred embodiment of the present invention comprises a cell unit U which is located adjacent a path of exhaust gas of an internal combustion engine and includes a sensor cell 5, a pump cell 1, a heater 7, and other elements to be described in more detail later.

Zirconia is used for the sensor cell 5, and the sensor cell 5 is located such that one of the walls thereof is exposed to a detecting chamber or cavity C1 into which exhaust gas is introduced through means of a diffusion hole 2 and which cooperates with the diffusion hole 2 so as to define a diffusion control means, while the other wall thereof is exposed to an atmospheric chamber C2 into which atmospheric air, used as a reference gas, is introduced. A sensor electrode 6 is located on the wall of the sensor cell 5 exposed to the detecting chamber C1, and a reference electrode 8 is located on the other wall of the sensor cell 5 which is exposed to the atmospheric chamber C2. It is to be noted that the sensor electrode 6 and the reference electrode 8 are made of platinum and each has a large number of fine holes or pores formed therein.

Figure 2:
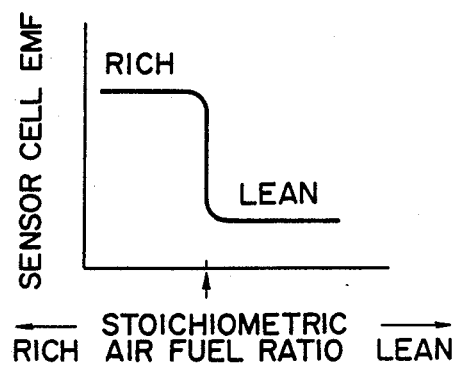
FIG. 2 is a graph illustrating the output characteristic of a sensor cell of the device of FIG. 1 as a function of the stoichiometric air fuel ratio.

With such a construction as described above, an electrical signal in the form of an electromotive force is generated between the electrodes 6, 8 of the sensor cell 5 in response to the difference between the concentration of oxygen in the exhaust gas introduced into the detecting chamber C1 and the concentration of oxygen in the atmospheric air introduced into the atmospheric chamber C2, or in other words, in response to the development of particular air fuel ratios, as graphically depicted within FIG. 2.

Zirconia is also used for the pump cell 1, and the pump cell 1 is located such that one of the walls thereof is exposed to the detecting chamber C1 while the other wall thereof is exposed to the path of the exhaust gas. A pair of pump electrodes 3A, 3B are located on the walls of the pump cell 1 and surround the entrance to and the exit from the diffusion hole 2, respectively. Also the pump electrodes 3A, 3B are made of platinum and each has a large number of fine holes or pores formed therein.

The pump cell 1 operates such that when the pump electrode 3A is positive, it ionizes oxygen within the detecting chamber C1 and pumps the ions out from the detecting chamber C1 and into the path of the exhaust gas, but on the contrary when the pump electrode 3A is negative, it ionizes oxygen in the path of the exhaust gas and pumps the ions out from the exhaust gas path and into the detecting chamber C1.

It is to be noted that the diffusion hole 2 is defined as a through-bore in the pump cell 1 and provides communication between the path of the exhaust gas and the detecting chamber C1.

The heater 7 is mounted on a partition wall located externally of the sensor cell 5 and on the side thereof which is opposite that side of the sensor cell 5 upon which is mounted sensor electrode 6 with an insulator layer 4 interposed therebetween. Thus, as power is supplied from a power source 7a to the heater 7, the entire cell unit U is heated by the heater 7. Since the cell unit U is heated to a temperature, for example, within the range of 600 to 700 degrees C., operation of the pump cell 1 and the sensor cell 5 is assured.

The sensor electrode 6 and the pump electrode 3B are grounded, and the reference electrode 8 is connected to an input terminal of a comparator 10 via an amplifier 9.

Connected to the other input terminal of the comparator 10 is a reference voltage source 10a the voltage value of which corresponds to an electromotive force level generator when the air fuel ratio of the air fuel mixture coincides with the stoichiometric air fuel ratio. Thus, the comparator 10 compares the output voltage Vs from the amplifier 9 with a reference voltage value signal Vref from the reference voltage source 10a and generates, when, for example, $Vs \geq Vref$, a signal of a high level (hereinafter referred to as a "Hi signal") but generates a signal of a low level (hereinafter referred to as a "Lo signal") when $Vs < Vref$. Thus, the comparator 10 generates a binary signal which is either a Hi signal or a Lo signal.

An integrating amplifier 11 with positive and negative power sources is connected within the system so as to receive a signal from the comparator 10. The integrating amplifier 11 serves as a controlling means with an inversion-type power source and integrates the signal from the comparator 10 with a negative coefficient and outputs the same when the signal remains at a Hi level, but on the contrary when the signal from the comparator 10 is at a Lo level, it integrates the signal with a positive coefficient and outputs the same accordingly. Thus, the integrating amplifier 11 outputs a negative or positive voltage which corresponds in duration to the Hi or Lo signal received from the comparator 10 and may, for example, increase in absolute value as the duration increases.

In this manner, an electrical control signal outputted from the integrating amplifier 11 with positive and negative power sources varies in polarity and duration in response to the output of the comparator 10 and its duration, respectively, and is supplied to the pump electrode 3A.

It is noted than an electrical control signal from the integrating amplifier 11 with positive and negative power sources contains information regarding the current air fuel ratio. Thus, an air fuel ratio detecting means is provided for detecting the air fuel ratio from control current flow which is transmitted from the integrating amplifier 11 to the pump cell 1. The air fuel ratio detecting means includes a first detecting means, that is a linear air fuel ratio detecting means, DM1 for detecting the magnitude of the control current flow so as to determine a linear air fuel ratio, and a second detecting means, that is, a stoichiometric air fuel ratio detecting means, DM2 for detecting the direction of the control current flow so as to determine the stoichiometric air fuel ratio. In particular, an air fuel ratio detecting resistor 17 serving as a control current flow detecting means is interposed in an electrical control signal supply line between the integrating amplifier 11 with positive and negative power sources and the pump electrode 3A of the pump cell 1. Signals $V_1$, $V_2$ from opposite ends of the resistor 17 are delivered to a comparator 15 of the second detecting means DM2.

The comparator 15 thus develops an output signal OUTPUT1, as the detection signal, which is a Hi signal when $V_1 - V_2 \geq 0$ and which is a Lo signal when $V_1 - V_2 < 0$.

Figure 3:
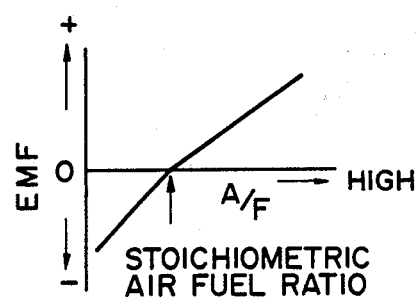
FIG. 3 is a graph illustrating the output characteristic of a voltage detecting circuit of the device of FIG. 1 as a function of the stoichiometric air fuel ratio.
Figure 4:
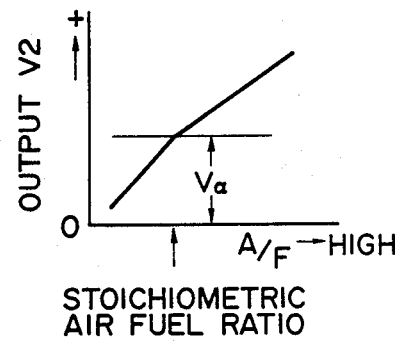
FIG. 4 is a graph illustrating the output characteristic of an adding circuit of the device of FIG. 1 as a function of the stoichiometic air-fuel ratio.

Meanwhile, the first detecting means DM1 develops an output signal OUTPUT2 as an air fuel ratio calculation signal V2 and includes the resistor 17, a voltage detecting circuit 12 for detecting a voltage across the resistor 17, and an adding or bias circuit 13 connected to the voltage detecting circuit 12. It is to be noted here that since the output of the voltage detecting circuit 12 can sometimes take a negative value as illustrated in FIG. 3, a bias value Vα is added to the output signal of the voltage detecting circuit 12 as seen in FIG. 4 by the adding circuit 13 in order that the output signal OUTPUT2 of the first detecting means DM1 may always assume a positive value.

Figure 5:
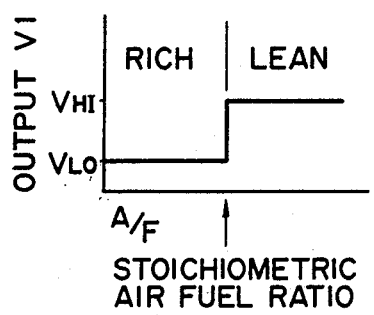
FIG. 5 is a graph illustrating the output characteristic of a second detecting means of the device of FIG. 1 as a function of the stoichiometric air-fuel ratio.
Figure 6:
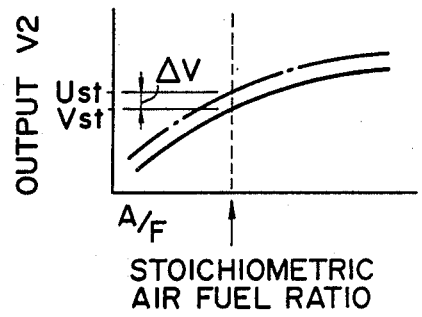
FIG. 6 is a graph illustrating the output characteristic of a first detecting means of the device of FIG. 1 as a function of the stoichiometric air fuel ratio.

The output signals OUTPUT2, OUTPUT1 of the first and second detecting means DM1, DM2 are delivered to a controller 19 which has the function of an air fuel ratio calculating means. The air fuel ratio calculating means first detects, from a detection signal V1 (output signal OUTPUT1) and an air fuel ratio calculation signal V2 (output signal OUTPUT2) as shown in FIGS. 5 and 6, respectively, the time at which the stoichiometric air fuel ratio is reached, and then calculates the difference $\Delta V$ between the air fuel ratio calculation signal $V_{ST}$ detected at the time and a preset stoichiometric air fuel ratio signal $U_{ST}$ stored in a storage means, that is, $\Delta V = (V_{ST} - U_{ST})$, and finally corrects, using a correcting means, the air fuel ratio calculation signal V2 in accordance with the difference $\Delta V$ in order to subsequently calculate an actual air fuel ratio A/F.

It is noted that the storage means which is included in the controller 19 stores therein the linear air fuel ratio value which is determined in a predetermined functional relationship with respect to the magnitude of the control current flow and that the correcting means which is also included in the controller 19 corrects the predetermined functional relationship when a stoichiometric air fuel ratio signal is developed from the stoichiometric air fuel ratio detecting means.

The controller 19 may be principally composed of a microcomputer and controls a fuel injection valve not shown of the engine so as to operate at a predetermined time and for an appropriate valve opening time or duty ratio.

Figure 7:
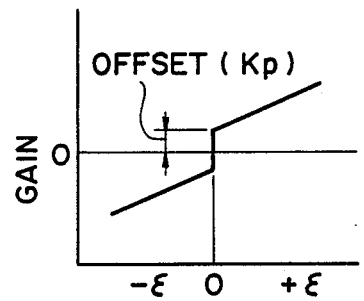
FIG. 7 is a graph illustrating the concept of a data map of the offset and proportional portions which are used in the calculation of a fuel amount correcting coefficient for the device of FIG. 1.
Figure 8:
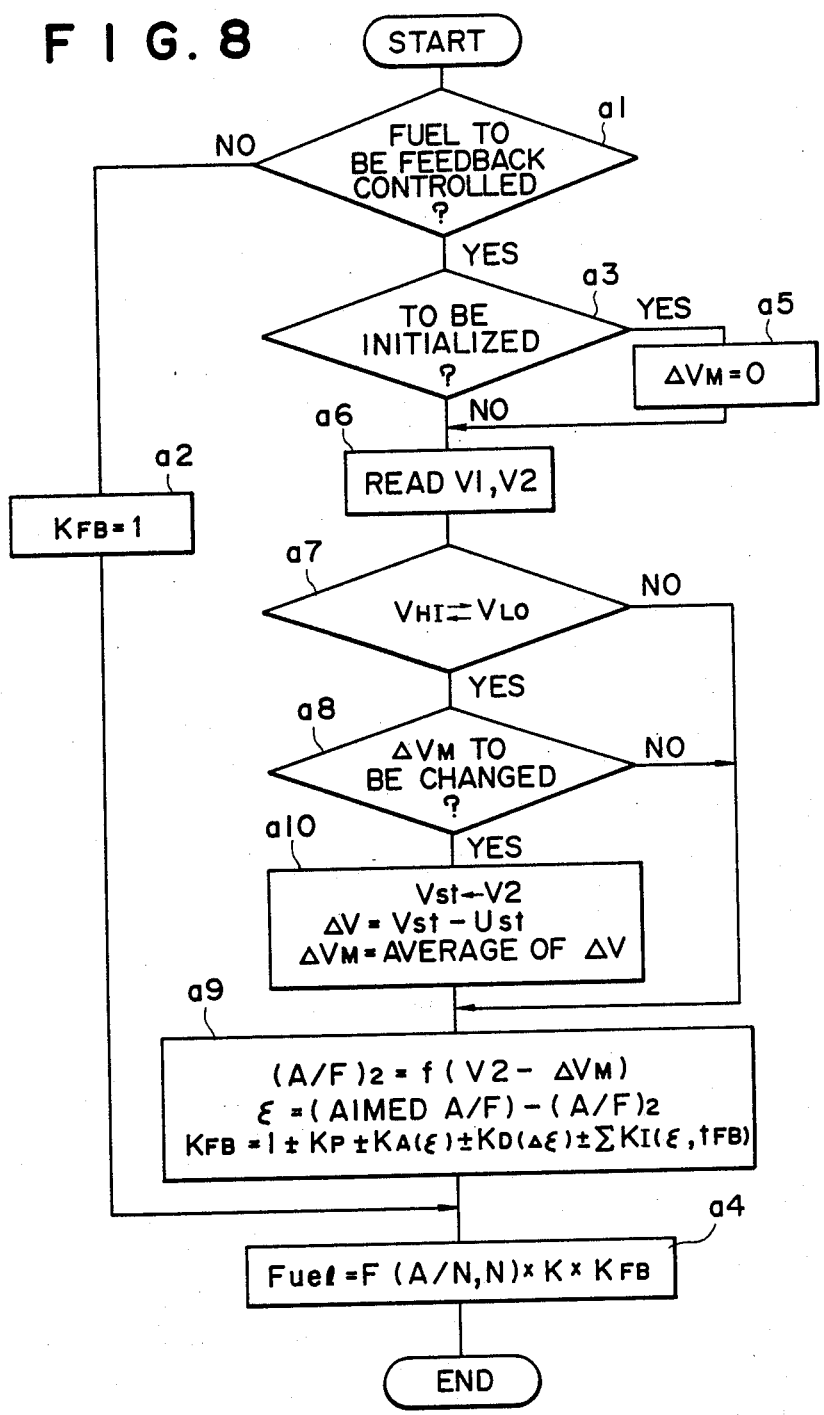
FIG. 8 is a flow chart of a control program for the device of FIG. 1.

In particular, the microcomputer includes a ROM (read only memory) in which a control program including a main routine, for causing the microcomputer to operate as an engine controller, as is well known in the art, and other required routines or subroutines, is stored. In the drawings, only a fuel amount calculating routine of the program is shown in FIG. 8. It is to be noted that a data map as illustrated in FIG. 7 from which feedback gains are calculated is stored in the ROM of the microcomputer.

Referring to FIG. 8, after the routine shown has been entered, the microcomputer first determines at step a1 whether or not a requirement for a feedback control, which is one of the fuel amount controlling modes, is met, or in other words, the microcomputer determines from an input signal from a temperature detecting means, which itself is well known in the art and therefore not shown in the drawings, whether or not the engine has completed its warming up mode on operation and accordingly the cell unit U is held at a predetermined temperature.

When the determination is in the negative as indicated "No" in FIG. 8, the sequence advances to step a2, but on the contrary when the determination is in the affirmative as indicated "Yes" in FIG. 8, the sequence advances to step a3. At step a2, the fuel amount correcting coefficient $K_{FB}$ for the proper air fuel ratio is set to 1, and then at step a4, the microcomputer calculates the fuel amount of duty ratio. Here at step a4, the microcomputer first calculates a reference fuel amount F (A/N, N) from data which has already been obtained in preceding routines in connection with the calculation of a suction air amount A/N and in connection with the calculation of an engine rotational frequency, which in connection with the parameters are themselves well known in the art and are both entered at predetermined time intervals in response to interruption requests, whereafter the reference fuel amount F thus calculated is multiplied by the fuel amount correcting coefficient $K_{FB}$ (=1 here), depending upon the air fuel ratio, and another fuel amount correcting coefficient K, depending upon some other factor or factors such as the atmospheric pressure, in order to determine the corrected fuel amount. Subsequently, the sequence returns to the main routine not shown. It is to be noted that either a suction air pressure parameter or a throttle opening parameter may be used in lieu of the suction air amount A/N.

Continuing further, at step a3, the microcomputer makes a determination regarding the necessity of whether or not an average $\Delta V_M$ of differences $\Delta V$ need to be initialized or cleared preceding the calculation of such an average $\Delta V_M$. Then when it is determined that such initialization is necessary, the sequence advances to step a5 at which the average $\Delta hd M$ is reset to zero, and the sequences advances further to step a6. Meanwhile, when it is determined at step a3 that such initialization is not necessary, the sequences advanced directly to step a6. At step a6, the microcomputer reads outputs V1, V2, that is, OUTPUT1 and OUTPUT2. Subsequently, the value V1 is compared at step a7, with a value of the output OUTPUT1, which was read in the preceding cycle, in order to determine whether or not the output OUTPUT1 exhibits a change from a Hi level to a Lo level, that is, $V_{Hi} \to V_{Lo}$ as seen in FIG. 5, which occurs when the stoichiometric air fuel ratio is reached. In case such a change is determined, the sequence advances to step a8, but otherwise, the sequence advances to step a9.

At step a8, since the air fuel mixture is at the stoichiometric air fuel ratio, the microcomputer makes a determination whether or not such a requirement is met for correction of the average difference value $\Delta V_M$, that is, for example, whether or not the change of the acceleration opening $\theta$ is smaller than a reference value $\alpha$ or whether or not the aimed air fuel ratio A/F has not just been changed. When there is no requirement for such modification, the sequence advances to step a9, but otherwise, the sequence advances to step a10.

At step a10, the output V2 of the adding circuit 13 is read as an actual value $V_{St}$ at a point in time when the stoichiometric air fuel ratio is reached, and then the difference $\Delta V$ of the value $V_{St}$ from a preset stoichiometric air fuel ratio signal $U_{St}$ is calculated (that is, $\Delta V = V_{ST} - U_{St}$), whereafter the value and a successive value or values of the difference $\Delta V$ obtained now and in a preceding cycle or cycles are averaged so as to obtain an average difference value $\Delta V_M$. Subsequently, the sequence advances to step a9.

At step a9, the air fuel ratio A/F is calculated. Here, the deviation of the air fuel ratio calculation signal V2 at a point of time is corrected with the average difference value $\Delta V_M$ (refer to FIG. 6) in order to determine the air fuel ratio in accordance with, for example, the equation $(A/F)_2 = f(V2 - \Delta V_M)$. By correcting the air fuel ratio calculation signal V2 with the average difference value $\Delta V_M$ (or else $\Delta V$), the errors in accuracy in the bias value $V\alpha$ of the adding circuit 13 which occur between products and due to aging can all be removed, and accordingly the air fuel ratio can be calculated at any time with a high degree of accuracy.

Subsequently, the difference $\epsilon$ between the aimed air fuel ratio A/F and the actual air fuel ratio is calculated, and the difference $\Delta\epsilon$ of the value $\epsilon$ from a preceding value of the difference $\epsilon$ is also calculated. Subsequently, a fuel amount correcting coefficient $K_{FB}$ for the air fuel ratio is calculated.

Here, a proportion term $KA(\epsilon)$ for the gain (refer to FIG. 7) depending upon the level of the difference $\epsilon$ calculated, and an offset amount KP with which a delay in the response of a ternary catalyzer not shown is to be prevented, are calculated, and then $KD(\Delta\epsilon)$ and $\epsilon KI(\epsilon,t_{FB})$ are calculated as differentiation and integration terms, respectively, subsequently those calculated values are added or subtracted in order to determine the fuel amount correcting coefficient $K_{FB}$.

Subsequently, the sequence advances to step a4 at which the fuel amount to be supplied at this point in time is calculated from the calculated fuel amount correcting coefficient $K_{FB}$, the correcting coefficient K and the reference fuel amount F (A/N, N). Subsequently, the sequence returns to the main routine.

In this manner, the air fuel ratio detecting device can calculate the air fuel ratio $(A/F)_2 = f(V_2 - \Delta V_M)$ with a high degree of accuracy by detecting from the output V1 of the second detecting means DM2 the time at which the stoichiometric air fuel ratio is reached, by detecting the output V2 of the first detecting means DM1 at such time as an output $V_{ST}$ corresponding to the actual stoichiometric air fuel ratio, by calculating the difference $\Delta V'(V_{St} - U_{St})$ between the output $V_{St}$ and the stoichiometric air fuel ratio signal $U_{St}$ which is stored in the microcomputer in advance, and then effecting a correction of the air fuel ratio calculation signal $V_2$ by subtracting $\Delta V_M$ (average value of $\Delta V$) upon calculation of an air fuel ratio in an entire air fuel ratio region. Consequently, calculation of a fuel supply amount conducted in accordance with the air fuel ratio thus obtained is improved in accuracy, the air fuel ratio can be prevented from going out of a control width (window width) upon operation of the engine at the stoichiometric air fuel ratio (that is, upon feedback control), and the ternary catalyzer can be effectively and fully utilized.

In the operation of the air fuel ratio detecting device described above, while the air fuel ratio is calculated after determining the average of the differences $\Delta V$ at step a10, it may otherwise be calculated directly using the last single difference $\Delta V$ in order to simplify the process.

As is apparent from the foregoing description, according to the present invention, it is possible, in calculation of an air fuel ratio, to eliminate an error component from the air fuel ratio calculating signal V2 of the first detecting means. Accordingly, an air fuel ratio can be obtained with a high degree of accuracy.

Obviously, many modifications and variations of the present invention are possible in light of the above teachings. It is therefore to be understood that with the scope of the appended claims, the present invention may be practiced otherwise than as specifically described herein.

What is claimed is:

1. An air fuel ratio detecting device, comprising:
   a sensor cell, for developing an electrical signal in response to the difference between the concentration of oxygen present in an exhaust gas after an air fuel mixture has been burned within a combustion chamber, and the concentration of oxygen present in a reference gas, including a sensor electrode located upon one of a pair of opposite side walls of said sensor cell which is exposed to a detecting chamber into which said exhaust gas is introduced, and a reference electrode located upon the other side wall of said sensor cell which is exposed to a reference chamber into which said reference gas is introduced;
   a controlling means for developing an electrical signal having a polarity determined from an output of said sensor cell;
   a pump cell, for moving oxygen ions in response to an electrical control signal received from said controlling means, having one of a pair of opposite side walls thereof exposed to a path of said exhaust gas from said combustion chamber and the other side wall thereof exposed to said detecting chamber, a diffusion hole formed within said pump cell so as to provide fluidic communication between said path of said exhaust gas and said detecting chamber, and a pair of pump electrodes located upon said opposite side walls thereof;
   a control current detecting means for detecting control current flow transmitted between said controlling means and said pump cell;
   a stoichiometric air fuel ratio detecting means for detecting the direction of said control current flow so as to determine the stoichiometric air fuel ratio;
   a storage means for storing therein a linear air fuel ratio value which is determined in a predetermined functional relationship with respect to the magnitude of said control current flow;
   a linear air fuel ratio detecting means for detecting the magnitude of said control current flow detected by said control current detecting means so as to compare said detected control current flow with said stored linear air fuel ratio value from said storage means; and
   a correcting means for correcting said predetermined functional relationship stored in said storage means when a stoichiometric air fuel ratio signal is developed from said stoichiometric air fuel ratio detecting means.

2. An air fuel ratio detecting device as claimed in claim 1, wherein said control current detecting means is a resistor interposed in an electrical control signal supply line extending from said controlling means to said pump cell.

3. An air fuel ratio detecting device as claimed in claim 2, wherein said linear air fuel ratio detecting means includes a voltage detecting circuit for detecting a voltage across said resistor, and an adding circuit for adding a bias value to the output of said voltage detecting circuit.

4. An air fuel ratio detecting device as claimed in claim 2, wherein:
   said stoichiometric air fuel ratio detecting means includes a comparator for receiving voltage signals from opposite ends of said resistor and for developing a binary signal in response to a difference between said voltage signals received.

5. An air fuel ratio detecting device as claimed in claim 1, wherein said controlling means includes a comparator for comparing an output of said sensor cell with a reference signal so as to develop a binary signal, and a control circuit for receiving said binary signal from said comparator so as to develop an increased or decreased output.

6. An air fuel ratio detecting device as claimed in claim 5, wherein:
   said control circuit comprises an integrating amplifier with positive and negative power sources which integrates said binary signal from said comparator with a positive coefficient and outputs the same when said binary signal is at one level and integrates said binary signal from said comparator with a negative coefficient and outputs the same when said binary signal is at another level.

7. An air fuel ratio detecting device as claimed in claim 1, wherein said pump electrodes are disposed around an entrance and an exit of said diffusion hole.

8. An air fuel ratio detecting device as claimed in claim 1 wherein:
one of the components of said sensor cell is made of zirconia.

9. An air fuel ratio detecting device as claimed in claim 1, wherein:
said sensor electrode and said reference electrode provided on said sensor cell are made of platinum.

10. An air fuel ratio detecting device as claimed in claim 1, wherein said sensor electrode, said reference electrode and each of said pump electrodes each has a plurality of pores formed therein.

11. An air fuel ratio detecting device as claimed in claim 1, wherein said detecting chamber, said reference chamber, said sensor cell and said pump cell comprise a single unit.

12. An air fuel ratio detecting device as claimed in claim 11, wherein said unit has a heater provided therefor.

13. An air fuel ratio detecting device as claimed in claim 1, wherein said reference chamber is constituted as an atmospheric chamber into which atmospheric air is introduced as said reference gas.

14. An air fuel ratio detecting device as set forth in claim 1, wherein:
one of the components of said pump cell is made of zirconia.

15. An air fuel ratio detecting device as set forth in claim 1, wherein:
said pump electrodes provided on said pump cell are made of platinum.

* * * * *